United States Patent [19]

Selvin et al.

[11] Patent Number: 5,622,821
[45] Date of Patent: Apr. 22, 1997

[54] LUMINESCENT LANTHANIDE CHELATES AND METHODS OF USE

[75] Inventors: Paul R. Selvin; John Hearst, both of Berkeley, Calif.

[73] Assignee: The Regents of the University of California, Oakland, Calif.

[21] Appl. No.: 269,162

[22] Filed: Jun. 29, 1994

[51] Int. Cl.$^6$ ..................................................... C12Q 1/68
[52] U.S. Cl. ................... 435/6; 540/1; 540/450; 540/451; 540/452; 540/455; 540/465; 540/467; 540/476; 546/1; 546/2; 546/22; 546/23; 546/24; 546/26; 546/61; 549/1; 549/3; 549/5; 549/13; 549/23; 549/200; 549/204; 549/206; 549/218; 549/220; 549/263; 549/273; 549/283; 435/7.1; 435/7.2; 435/810; 436/501; 436/546; 436/536; 436/56; 436/63; 436/73; 436/81; 436/82; 436/164; 436/172; 436/800; 436/805; 530/300; 530/350; 536/22.1; 536/23.1; 536/24.3; 536/24.31; 536/24.32; 536/24.33; 935/77; 935/78

[58] Field of Search ..................... 435/6, 7.1, 7.2, 435/810; 436/501, 546, 536, 56, 63, 73, 81, 82, 164, 172, 800, 805; 530/300, 350; 536/22.1, 23.1, 24.3–24.33; 540/1, 450, 451, 452, 455, 465, 467, 476; 546/1, 2, 22, 23, 24, 26, 61; 549/1, 3, 5, 13, 23, 200, 204, 206, 218, 220, 263, 273, 283; 935/77, 78

[56] References Cited

U.S. PATENT DOCUMENTS

| 4,421,654 | 12/1983 | Plueddemann | 210/698 |
| 4,637,988 | 1/1987 | Hinshaw et al. | 436/546 |
| 4,794,191 | 12/1988 | Hinshaw et al. | 549/211 |
| 4,801,722 | 1/1989 | Hinshaw et al. | 549/211 |
| 4,837,169 | 6/1989 | Toner | 436/546 |
| 5,021,567 | 6/1991 | Johnson et al. | 540/470 |
| 5,252,462 | 10/1993 | Drevin et al. | 435/18 |

FOREIGN PATENT DOCUMENTS

8910975  11/1989  WIPO.

OTHER PUBLICATIONS

Ando et al., "Synthesis of a Highly Luminescent Terbium Chelate and its Application to Actin", *Biochimica et Biophysica Acta* 1102:186–194 (1992).

Baily et al., "Terbium Chelate for Use as a Label in Fluorescent Immunoassays", *Analyst* 109:1449–1450 (1984).

Canfi et al., "Fluorescent Terbium Chelates Derived From Diethylenetriaminepentaacetic Acid and Heterocyclic Compounds", *Analyst* 114:1405–1406 (1989).

Clark et al., "A Study of Sensitized Lanthanide Luminescence in an Engineered Calcium–Binding Protein", *Analytical Biochemistry* 210:1–6 (1993).

(List continued on next page.)

*Primary Examiner*—Ardin H. Marschel
*Attorney, Agent, or Firm*—Richard Aron Osman

[57] ABSTRACT

The invention provides lanthanide chelates capable of intense luminescence. The celates comprise a lanthanide chelator covalently joined to a coumarin-like or quinolone-like sensitizer. Exemplary sensitzers include 2- or 4-quinolones, 2- or 4-coumarins, or derivatives thereof e.g. carbostyril 124 (7-amino-4-methyl-2-quinolone), coumarin 120 (7-amino-4-methyl-2-coumarin), coumarin 124 (7-amino-4-(trifluoromethyl)-2-coumarin), aminomethyltrimethylpsoralen, etc.

The chelates form high affinity complexes with lanthanides, such as terbium or europium, through chelator groups, such as DTPA. The chelates may be coupled to a wide variety of compounds to create specific labels, probes, diagnostic and/or therapeutic reagents, etc. The chelates find particular use in resonance energy transfer between chelate-lanthanide complexes and another luminescent agent, often a fluorescent non-metal based resonance energy acceptor. The methods provide useful information about the structure, conformation, relative location and/or interactions of macromolecules.

18 Claims, 4 Drawing Sheets

OTHER PUBLICATIONS

Diamandis, "Europium and Terbium Chelators as Candidate Substrates for Enzyme–labelled Time–resolved Fluorimetric Immunoassays", *Analyst* 117:1879–1884 (1992).

Georges and Ghazarian, "Study of Europium–sensitized Fluorescence of Tetracycline in a Micellar Solution of Triton X–100 by Fluorescence and Thermal Lens Spectrometry", *Analytica Chimica Acta* 276:401–409 (1993).

Mathis, "Rare Earth Cryptates and Homogeneous Fluoroimmunoassays with Human Sera", *Clin. Chem.* 39(9):1953–1959 (1993).

Saavedra and Picozza, "Time–resolved Fluorimetric Detection of Terbium–labelled Deoxyribonucleic Acid Separated by Gel Electrophoresis", *Analyst* 114:835–838 (1989).

Saha et al., "Time–Resolved Fluorescence of a New Europium Chelate Complex: Demonstration of Highly Sensitive Detection of Protein and DNA Samples", *J. Am. Chem. Soc.* 115(23):11032–11033 (1993).

Selvin et al., "Improved Fluorescence Energy Transfer Using Lanthanide Chelates", *Biochemical Spectroscopy*, a volume of Methods in Enzymology, Academic Press, Ed. Kenneth Sauer, vol. 246, pp. 300–334 (1995).

Seveus et al., "Time–resolved Fluorescence Imaging of Europium Chelate Label in Immunohistochemistry and In Situ Hybridization", *Cytometry* 13:329–338 (1992).

von Brenndorff et al., "Soft X–ray Stimulated High Resolution Luminescence Microscopy", *Proceedings*, 4th Intn'l Conf on X–ray Microscopy, Chernogolovoka, Moscow District, Russia (1993).

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CCACTCTAGG                                                                    10
```

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
CCACTGGCTA GG                                                                 12
```

(2) INFORMATION FOR SEQ ID NO:3:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

CCACTGCTGC TAGG 14

(2) INFORMATION FOR SEQ ID NO:4:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

CCTAGAGTGG 10

(2) INFORMATION FOR SEQ ID NO:5:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Arg Glu Ser Gln Asn Tyr Pro Ile Val Lys Arg
1               5                   10

LUMINESCENT LANTHANIDE CHELATES AND METHODS OF USE

The research carried out in the subject application was supported in part by grants from the National Institutes of Health and the Office of Energy Research. The government may have rights in any patent issuing on this application.

INTRODUCTION

1. Field of the Invention

The field of this invention is luminescent lanthanide chelators.

2. Background

Luminescent (including fluorescent and phosphorescent) markers find a wide variety of applications in science, medicine and engineering. In many situations, these markers provide competitive replacements for radiolabels, chromogens, radiation-dense dyes, etc. Improvements in fluorimetric instrumentation have increased attainable sensitivities and permitted quantitative analysis.

Perhaps the single-most significant limitation to the use of luminescent markers is generating an acceptable signal-to-noise ratio. Marker-dependent properties such as absorbtion and emission maxima, Stoke's shift, quantum yield, etc. effect the ease of distinguishing signal from auto- or background fluorescence. Hence, there is a continuous need to provide improved luminescent markers; especially luminescent markers with long-lived luminescenee and/or a large Stokes shifts with long wavelenght emmissions. Other useful and desireable properties include: easy and cost-effective synthesis; chemical stability, especially in an aqueous environment; convenient attachability to a wide variety of macromolecules including proteins and nucleic acids; efficient excitability by a convenient laser; capable of intense luminescence; the capacity to perform as good luminescent resonance-energy transfer donors, enabling the determination of molecular distances beyond 100 Å; and usefulness as radiation-hardened fluorophores in X-ray microscopy.

RELEVANT LITERATURE

Relevant patents include U.S. Pat. Nos. 4,637,988 (1987) and 4,837,169 (1989). For a patent application using lanthanide cryptates as energy transfer donors, see U.S. Pat. Ser. No. 07/729,228, filed Jul. 12, 1991.

DTPA-pAS-Tb is reported in Bailey etak (1984) Analyst 109, 1449–1450. For background papers on other lanthanide chelators, see Diamandis (1992) Analyst 117, 1879–1884, Canfi et al. (1989) Analyst 114, 1405–1406, Ando et al. (1993) Biochimica et Biophysica Acta. 1102, 186–194, Georges and Ghazarian (1993) Analytica Chimica Acta, 276, 401–409, Mathis et at. (1993) Clin. Chem, 39, 1953 and Desai et al. (1993) J. Am. Chem. Soc. 115, 11032, Seveus et at. (1992) 13, 329–338, Saavedra and Picozza (1989) Analyst 114, 835–838 von Brenndorff et at. (1993) in Proceedings, 4th Intnl Conf on X-ray Microscopy, Chernogolovoka, Moscow District, Russia, Clark et at. (1993) Analytical Biochemistry 210, 1–6.

For an up-to-date review of Fluorescent Resonance Energy Transfer, see, Selvin (1994) Fluorescence Resonance Energy Transfer, in Biochemical Spectroscopy, a volume of Methods in Enzymology, Academic Press, Ed. Kenneth Sauer, in press (copy attached).

SUMMARY OF THE INVENTION

The invention provides lanthanide chelates comprising a lanthanide chelator covalently joined to a polynuclear heterocyclic aromatic sensitizer of the general formula:

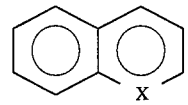

where X comprises an atom from periodic group 5 or 6.

In preferred chelates, the sensitizer has a first position 2–8 carbon atom substituted with an oxygen atom through a double covalent bond, a second position 2–8 carbon atom, different than the first position 2–8 carbon atom, substituted with a linking group through which the sensitizer is covalently joined to the chelator, and a substituted third position 2–8 carbon atom, different from the first and second position 2–8 carbon atoms. Frequently, the first position 2–8 carbon atom is the position 2 or 4 carbon atom, the second carbon atom is the position 7 carbon atom, the sensitizer and chelator are linked through an amine or carboxyl group, and/or the third position 2–8 carbon atom is the position 4 carbon and is substituted with a hydrocarbon or halogen substituted hydrocarbon. Exemplary sensitizers include 2- or 4-quinolones, 2- or 4- coumarins, or derivatives thereof e.g. carbostyril 124 (7-amino-4-methyl-2quinolone), coumarin 120 (7-amino-4-methyl-2-coumarin), coumarin 124 (7-amino-4-(trifiuoromethyl)-2-coumarin), aminomethyltrimethylpsoralen, etc.

The chelates are capable of forming high affinity complexes with lanthanides, such as terbium or europium, through chelator groups, such as DTPA. Typically, the chelators comprise a plurality of structurally constrained anionic groups such as carboxylate or phosphonate groups. Solutions of chelate-lanthanide complexes are capable of intense luminescence. The chelates may be coupled to a wide variety of compounds to create specific labels, probes, diagnostic and/or therapeutic reagents, etc.

Chelate-lanthanide complexes are useful as detectable labels in a wide variety of applications. Generally, the methods involve contacting a sample portion with a luminescent complex; exposing the sample portion to light at a first wavelength capable of inducing a first electronic transition in the chelate; and detecting an emission of light from the sample portion at a second wavelength that is longer than the first wavelength and results from a second electronic transition in the chelate. Specific analytes in the sample may be detected by coupling the chelate to a reagent capable of analyte selectively binding.

The chelates also find use in resonance energy transfer between chelate-lanthanide complexes and another luminescent agent, often a fluorescent non-metal based resonance energy acceptor. For example, by coupling the chelate-lanthanide complex donor to one atom and the acceptor to a second atom, the distance between two atoms can be measured. Generally, the spectral overlap of the donor emission and acceptor absorption is sufficient to enable energy transfer from donor to acceptor as measured by detectable quenching of donor luminescence intensity of lifetime or detectable increase in acceptor luminescence.

Where the atoms are on the same molecule, the methods provide useful information about the structure or conformation of the molecule. For example, the methods are used to monitor the status of a polymerase chain reaction by coupling the donor and acceptor to separated atoms of a diagnostic oligonucleotide. As the concentration of target DNA increases, the percentage of diagnostic oligonucleotides hybridized to target DNA increases which in turn increases the mean distance between the labelled atoms. This increased mean distance is detected as a decrease in energy transfer between the donor and acceptor. Where the atoms are on different molecules, the methods provide useful information on the interactions or relative locations of the two molecules.

DESCRIPTION OF SPECIFIC EMBODIMENTS

Figure 1:
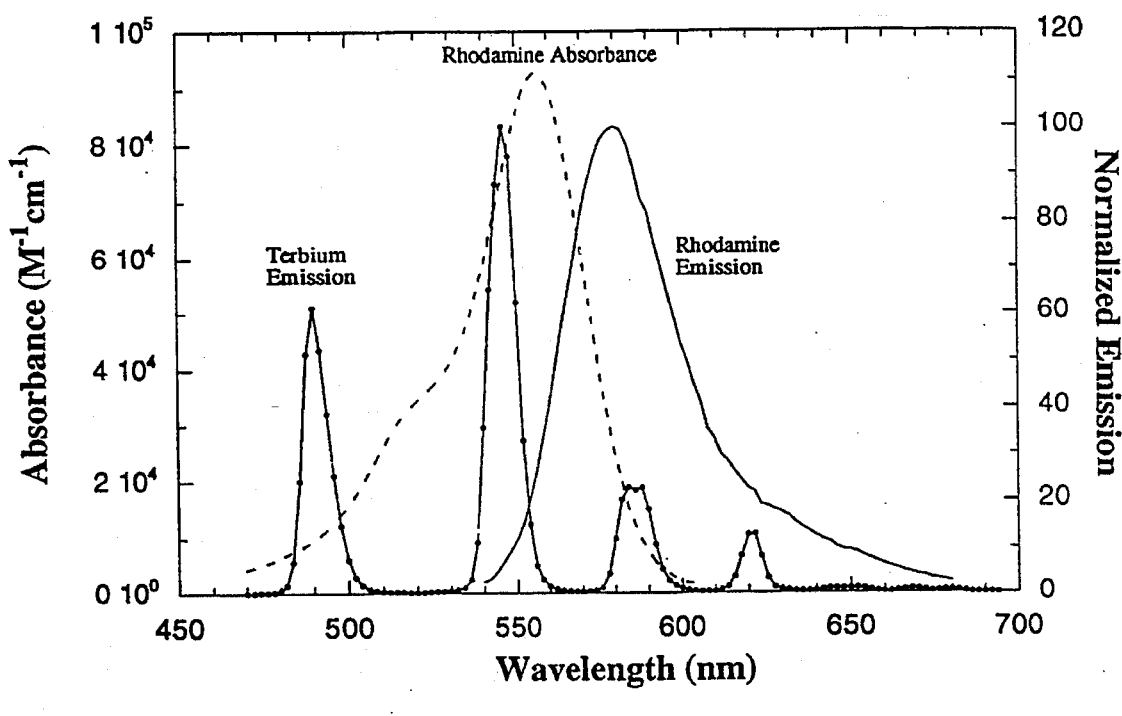
FIG. 1: Spectra of DNA labelled with either TMR or DTPA-cs124-Tb. Dashed and solid lines are the absorption and emission spectra of TMR, respectively. Solid line with circles is the emission spectrum of DTPA-cs124-Tb on DNA. The TMR emission spectrum shown above was obtained on a steady-state fluorimeter. The spectral overlap between terbium emission and TMR absorption enables energy transfer to take place.

We have synthesized a series of new chemical compounds which bind to lanthanide elements including terbium and europium, and efficiently sensitize them, i.e. allow them to be excited efficiently and subsequently luminesce efficiently. The compounds also enable convenient coupling to macromolecules. We call these compounds lanthanide chelates.

The importance of the invention is several-fold: First, our lanthanide chelates can be used as non-isotopic replacements for radioactive labels. Second, they can be used as alternatives to conventional fluorescent dyes, especially in imaging applications, with the potential for increased contrast. This increased contrast arises because the lanthanide luminescence is extremely long (0.6–2.3 millisecond). If one uses a pulsed excitation source and gated (time-resolved) detection, the intense autofluorescence (background) will decay away, with the labels still emitting. Such autofluorescence currently prevents fluorescent images of many tissue samples. Third, because the chelates are all excited in the same spectral region, two color imaging is possible. Fourth, the lanthanide chelates can be used as extremely efficient donors in luminescent energy transfer analyses. This use enables measurements of distances beyond 100 Å, distances currently not measurable with standard fluorescence energy transfer techniques, but of importance in structural biology and medicine.

Our chelates have a number of important advantages: 1. They are easy to synthesize and attach to macromolecules; 2. They are efficiently excited by a nitrogen laser (at 337 nm); 3. Some of of them (e.g. DTPA-cs124) can sensitize both terbium and europium; 4. The lanthanide luminescence from the chelates are extremely intense; for example, the terbium chelate exemplified below luminesces approximately sixty-five times more intensely than DTPA-paraminosalycilate (DTPA-pAS) when excited at 337 nm; 5. They are chemically stable; 6. They can be used to label nucleic acids and proteins under chemical conditions used in automated synthesizers (e.g. creating phosphoramidites in DNA/RNA technology or protein technology); 7. They are extremely good resonance energy transfer donors. An important element in the success of our chelates in energy-transfer is the fact that there is very little spectral or temporal overlap between the sensitizer's emission and the lanthanide's emission. In contrast, DTPA-pAS has very significant temporal and spectral overlap and provides a poor energy transfer donor; and, 8. They are useful as radiation-hardened fluorophores in X-ray microscopy.

Our lanthanide chelates comprise a polynuclear heterocyclic aromatic sensitizer of the general formula:

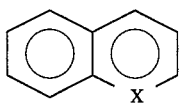

where X comprises an atom from periodic group 5 or 6.

Suitable sensitizers may include a variety of additional structure including structures where the above general formula comprises a structurally minor portion of the sensitizer. Generally, at least one of the position 2–8 carbon atoms, preferably position 2 or 4, is oxidized, preferably to a carbonyl (i.e. double bonded to an oxygen atom). Positions are conventionally numbered: counter-clockwise from the heteroatom which is position number 1. Frequently, another position 2–8 carbon atom, preferably the other 2 or 4 position, is substituted (i.e. a hydrogen atom is replaced) with a group comprising an alkyl, vinyl, oxy (including hydroxyl, alkoxy, carboxyl), carbonyl or substituted nitrogen (e.g. nitro-, amino including substituted amines, etc.), cyano, acetate, etc. group, or a derivative thereof, particularly halide derivatives. Exemplary sensitizers include rhodamine 560, 575 and 590 fluoresceins, 2- or 4-quinolones, 2 or 4- coumarins, or derivatives thereof e.g. coumarin 445, 450, 490, 500 and 503, 4-trifluoromethylcoumarin (TFC), 7-diethyl-amino-cumarin-3-carbohyddzide, etc., and especially carbostyril 124 (7-amino-4-methyl-2-quinolone), coumarin 120 (7-amino-4-methyl-2-coumarin), coumarin 124 (7-amino4-(trifluoromethyl)-2-coumarin), aminomethyltrimethylpsoralen:

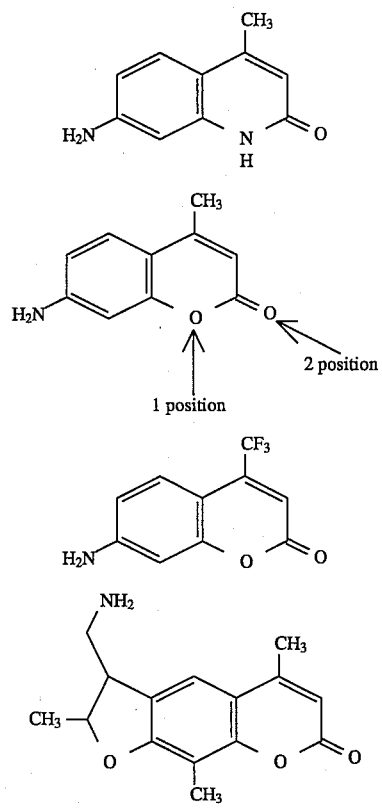

A wide variety of derivatives of the above general formula may be used as sensitizers, so long as the resultant chelate provides the requisite lanthanide binding and luminescence enhancement. By enhanced luminescence is meant that a solution of the chelate complexed with a lanthanide, when exposed to light at a wavelength, the complexed lanthanide emits light of greater intensity or lifetime than an identical sample absent the chelate. The enchancement is usually at least 50%, preferably at least 500%, more preferably at least 5000%, most preferably at least 50,000% greater intensity under at least one set of conditions (e.g. specified concentration, solvent system, etc.) e.g. see conditions described herein.

To effectively excite the resident lanthanide, the chelates generally provide absorbtion maxima between 150 and 750 nm, usually between 200 and 650 nm, more usually between 250 and 550 nm, most usually between 300 and 450 nm. Generally, detected emissions are at least 50 nm, usually at least 100 nm, more usually at least 150 nm greater than the incident light. For example, preferred detected emissions for terbium and europium are 492 and 546 nm and 617 and 695 nm, respectively. Extinction coefficients generally exceed 5,000, usually 8,000, more usually 11,000.

The selection of particular chelator-sensitizer combinations is dependent on the intended application. Criteria include the selected lanthanide, sources of potential background fluoresence, quenching agents, the incident light source, etc. Functionally, suitable chelates for a given lanthanide are identified by coupling a candidate sensitizer to a chelator such as DTPA, complexing with the lanthanide, and identifying complexes capable of enhanced lanthanide luminescent. Assay details are described below.

The chelates are capable of forming high affinity complexes with lanthanides, such as terbium or europium. The chelates bind at least one lanthanide, preferably at least one of terbium and europium, with an equilibrium constant of at least $10^6 M^{-1}$, preferably at least $10^8 M^{-1}$, more preferably at least $10^{10} M^{-1}$ under at least one set of conditions described herein. A wide variety of structural moieties can be used to provide the requisite lanthanide binding affinity, so long as the resultant chelate provides the requisite luminescence. However, the lanthanide is usually ionically bound by anionic groups such as carboxylate or phosphonate groups.

Frequently, the chelates comprise one or more structurally distinct chelator portions. Typically, these chelator portions comprise a plurality of structurally constrained anionic groups such as carboxylate or phosphonate groups. In a preferred embodiment, these portions are selected from compounds which themselves are capable of functioning as lanthanide chelators with the aforementioned binding affinities. For example, such chelator portions include EDTA, DTPA, DOTA, NTA, HDTA, etc. and their phosphonate analogs such as DTPP, EDTP, HDTP, NTP, etc. The chelate's lanthanide affinity may also be a cooperative (synergistic) result of the interaction of a plurality of functional groups. For example, one or more amino acids moieties, e.g. glycine, of the chelate can be structurally positioned to bind vacant coordination sites of the lanthanide to enhance overall binding affinity.

Where the chelate comprises a structurally distinct chelator portion, it is usually covalently joined to the sensitizer portion, typically through a linking group. Any linking group that is capable of covalently linking the sensitizer with the chelator and does not preclude requisite lanthanide binding and luminescence may be used. Thus, the linking group may comprise a wide variety of structures. Frequently, the linking group comprises a nitrogen, carboxyl, carbonyl or alcohol group or a nitrogen or carboxyl derivative and is covalently joined to a position 2–8 carbon atom in the general formula. The linking group is often covalently joined to one of the position 2–8, frequently position 7, carbon atoms above. Common linking groups are aliphatic and aromatic amines, which may be primary or secondary, carboxyls and sulfhydryls. The chelator and sensitizer are frequently joined through an amide, anhydride, disulfide, thio-urea, thioether, etc. bond.

The chelates may be synthesized in any convenient way. Many of the disclosed sensitizers and chelators sensitizers are commercially available—others are synthesized or modifed from commercial starting materials according to conventional methods. The two may be coupled by any convenient chemistry, though they are most often directly coupled through functional groups as described herein. For example, some of the preferred chelates are based on a reaction between an anhydride (e.g of diethylenetriaminepentaacetic acid, caDTPA) and a sensitizer (the DTPA acts as the chelator, binding the lanthanide tightly and preventing radiationless deactivation by water, and the organic compound acts as a sensitizer, allowing efficient excitation of the lanthanide). These chelates may be made by a modification of the procedure of Bailey et al (1984) Analyst 109, 1449–1450, where an amine-containing sensitizers replace pAS. The anhydride of DTPA are separately dissolved in an anhydrous organic solvent, typically dry dimethylsulfoxide. The anhydride and selected sensitizer are then mixed and allowed to react for approximately an hour. The anhydride reacts with the amine on the sensitizer to form a stable amide bond.

Where desired, the chelate may be coupled to an analyte-specific reagent, organic polymer, macromolecule (esp. biomolecules like nucleic acids and proteins), etc in any convenient way. For example, for covalent coupling to a protein (or other amine containing macromolecule), the chelate can be originally formed using the dianhydride of DTPA. After coupling to the sensitizer, the mixture is then added to the amine-containing macromolecule, either in an organic solvent or in an aqueous solvent. The second dianhydride then reacts with the amine(s) on the macromolecule, forming another amide bond. The reactivity of the amine is sufficiently great that this reaction can be done in an aqueous medium (even though water competes for reaction with the anhydride).

Alternatively, a bifunctional linker can be used to couple the chelate and the macromolecule. For example, a suitable linker may comprise both a thiol reactive group (e.g. maleinide, acetyl halide, etc.) and an amine reactive group (e.g. thiourea, isothiocyanate, etc. ). For instance, the monoanhydride of DTPA may be coupled to a protein by reacting with 3-(2-pyridyldithio)propionyl hydrazide (PDPH).

Chelate-lanthanide complexes are useful as detectable labels in a wide variety of applications. Generally, the methods involve contacting a sample potion with a luminescent complex of a chelate and a lanthanide; exposing the sample portion to light at a first wavelength capable of inducing a first electronic transition in the chelate; and detecting, advantageously with a time delay to minimisze the detection of shorter-lived background luminescence, an emission of light from the sample portion at a second wavelength that is longer than the first wavelength and results from a second electronic transition in the chelate. Specific analytes in the sample may be detected by coupling the chelate to a reagent capable of analyte selectively binding.

The methods are adaptable to a wide variety of samples including biological samples and extracts (such as physiological fluids, nucleic acid and/or proteinaceous solutions, microbial cultures, etc.), environmental samples (such as water sources), industrial, especially chemical reagents, products and wastes, etc. The chelates may be free in solution or restrained in a variety of ways. For example, the chelates may be preferentially partitioned in or on one phase, solid or liquid, such as adsorbed onto a solid surface or membrane or retained within a bead (e.g. latex microspheres). Thus, the methods are useful in conjunction with sorting (e.g. cell sorting), chromatography, electrophoretic, osmotic and centrifugal separations. Heat and organo-stable chelates are selected for applications involving elevated temperature (e.g. distillations, combustions, etc.) and organic extractions.

The first wavelength (that of the incident light) is selected to optimize the ultimate signal-to-noise ratio of the lanthanide emission. Frequently, the incident light is provided in a form to minimize background absorption. Useful sources include lasers (e.g. nitrogen, helium-cadmium, dye lasers, etc.) and are lamps (e.g. high-pressure, mercury, xenon, quartz, etc.). Nitrogen lasers are particularly preferred because their 337 nm emission frequency is close to a lanthanide absorbtion maximum. Similarly, the second wavelength is selected to optimize signal-to-noise ratio and in view of the available instrumentation.

The subject chelates may be coupled to a wide variety of compounds to create specific labels, probes, diagnostic and/or therapeutic reagents, etc. Examples include biomolecules such as proteins (antibodies, enzymes, receptors, etc.), nucleic acids (RNA, DNA, etc.), bioactive molecules (drugs, toxins, etc.); solid subtrates such as glass or polymeric beads, sheets, fibers, membranes (e.g. nylon, nitrocellulose), slides (e.g. glass, quartz) and probes; etc.

Many of our ehelates are particularly amenable to what we term Luminescence Resonance Energy Transfer, or LRET. LRET is a generalized version of Fluorescent Resonance Energy Transfer, or FRET, a widely used technique in polymer science, biochemistry and structural biology. FRET can be used to measure the distances between two points that are labelled with fluorescent dyes and separated by approximately 10–75 Å. The technique is valuable because measurements can be made under physiological (or other) conditions with near-Angstrom resolution and with the exquisite sensitivity of fluorescence measurements. FRET relies on a distant-dependent transfer of energy from one fluorescent dye—the donor—to another absorbing or fluorescent dye—the acceptor. The donor and acceptor are site-specifically placed at the two points that one wishes to measure the distance between.

While lanthanides do not fluoresce, the use of our chelates permits them to be efficiently excited. A non-fluorescent quantum transition of the lanthandide can then effect a non-radiative energy transfer to a suitable and appropriately distanced acceptor. To effect transfer, an acceptor absorbtion must overlap a lanthanide emission. The chelate—acceptor pair is selected for optimal overlap: for longer distance measurements, greater overlap is preferred. Since the lanthanides have lifetimes on the order of a millisecond, the signal-to-noise ratio of sensitized emission of the acceptor in LRET is improved by emission detection through time resolution (pulse delay) or phase modulation. Energy transfer can be detected by donor quenching or, preferably acceptor luminescense.

By using luminescent lanthanide chelators as donors (instead of conventional dyes), and conventional fluorescent dyes as acceptors, we have improved the signal to background of LRET by approximately 100-fold. This improvement allows measurements beyond 100 Å, a distance currently unmeasurable using small, conventional fluorescent dyes. This distance regime is important in many biological problems. Using lanthanide chelators as donors also makes distance measurements more accurate, because the chelators minimize the uncertainty in the orientation-dependence of energy transfer. We have also demonstrated the first lifetime measurement of the sensitized emission of the acceptor, a LRET measurement which eliminates problems associated with non-specific or incomplete labelling.

A wide variety of acceptors are useful with our chelate donors. Generally, the selected acceptor will have an absorbance maximum at a wavelength between 25 nm and 250 nm longer than that of the donor chelate. Exemplary acceptors include xanthene dyes such as fluoresceins and rhodamines, coumarins, benzimide dyes, phenanthridine dyes, ethidium dyes, acridine dyes, cyanine dyes such as thiazole orange, thiazole blue, Cy5, Cy5.5, Cy3, etc., carbazole dyes, phenoxazine dyes, porphyrin dyes, quinolone dyes, pycobillyc proteins, e.g. allophycocyanin, R-phycoerythrin, B-phycoerythrin, Bodipy dyes, etc. The acceptors generally emit in the visible or infrared ranges.

LRET is particularly useful to obtain structural and kinetic information about macromolecules in solution, in real time. For example, double-end labeled oligonucleotides provide detectable LRET signalling when bound by nucleic acid binding proteins, e.g. transcription factors. Accordingly, the methods are used to screen for potential therapeutics that alter the structure or interactions of biomolecules; for example, anti-viral agents are sceened for the ability to alter vital transcription factor-induced alterations in nucleic acid conformation.

The general LRET-based method of detecting the distance between a first position and a second position in a portion of a sample involves: exposing a sample portion comprising the donor lanthanide-chelate complex located at the first position and the acceptor located at the second position to light at a first wavelength capable of inducing a first electronic transition in the donor. The spectral overlap of the donor emission and acceptor absorption is sufficient to enable energy transfer from the donor to the acceptor as measured by detectable quenching of donor luminescence intensity or lifetime or detectable increase in acceptor luminescence intensity or lifetime. Then the intensity of a first emission of light from the sample portion at a second wavelength is detected wherein the second wavelength is longer than the first wavelength and results from a second electronic transition in the donor, wherein the intensity of the first emission of light correlates with the distance between the first and second positions. In other words, the closer the positions, the greater the energy transfer and the greater the donor quenching. Alternatively, one can detect the intensity of a second emission of fight from sample portion at a third wavelength, wherein the third wavelength is longer than the first wavelength and results from an electronic transition in the acceptor, wherein the intensity of the second emission of light inversely correlates with the distance between the first and second postions of the sample portion. In other words, the closer the positions, the greater the energy transfer and the greater the acceptor luminescense.

This general method has broad application whenever the static or dynamic distance between to positions, e.g. two atoms or molecules, is of interest. In one specific embodiment, the method is used to monitor the status of a polymerase chain reaction. Here, the sample portion comprises a target nucleic acid strand comprising a first strand portion and a diagnostic nucleic acid strand labeled proximal to one end with the acceptor and proximal to the other end with the donor (i.e. comprising a first atom covalently joined to the donor and a second atom covalently joined to the acceptor, the first and second atoms being separated by a second strand portion). The first and second strand portions are sufficiently complementary to hybridize under annealing conditions, and the second strand portion is of sufficient length to provide a detectable difference in the aggregate energy transfer from the donor to the acceptor when the first and second strand portions are hybridized as compared with the aggregate energy transfer from the donor to the acceptor when the first and second strand portions are not hybridized. The detectable difference is measured as at least one of a detectable quenching of donor luminescence or detectable increase in acceptor luminescence, and the distance between the first and second atoms indicates whether the nucleic acid strands have hybridized. Thus, as the reaction proceeds, the stepwise increase in the mount of target nucleic acid is reflected in a stepwise decrease in energy transfer.

The following examples are offered by way of illustration and not by way of limitation.

EXAMPLES

Example 1

In this example, we exemplify the technique of luminescent resonance energy transfer (LRET) by introducing a luminescent terbium chelate as a donor, and an organic dye, tetramethylrhodamine, as acceptor. The results are consistent with a Förster theory of energy transfer, provided the appropriate parameters are used. The use of lanthanide donors, in general, and this pair, in particular, has many advantages over more conventional FRET pairs which rely solely on organic dyes. The distance at which 50% energy transfer occurs ($R_o$) is large, 65 Å; the donor lifetime is single exponential and long (millisecond), making lifetime measurements facile and accurate; uncertainty in the orientation factor ($\kappa^2$) which creates uncertainty in measured distances is minimized by the donor's multiple electronic transitions and long lifetime; the sensitized emission of the acceptor can be measured with little or no interfering background, yielding a >25 fold improvement in signal to background over standard donor-acceptor pairs. These improvements are expected to make distances greater than 100 Å measurable via LRET. We also report measurement of the sensitized emission lifetime, a measurement which is completely insensitive to total concentration and incomplete labeling.

In FRET a fluorescent donor molecule transfers energy via a non-radiative dipole—dipole interaction to an acceptor molecule (which is usually a fluorescent molecule). FRET is a standard spectroscopic technique for measuring distances in the 10–70 Å range. Upon energy transfer, which depends on the $R^{-6}$ distance between the donor and acceptor, the donor's lifetime and quantum yield are reduced, and the acceptor fluorescence is increased, or sensitized(1). FRET is frequently used in both polymer science and structural biology and has recently been used to study macromolecular complexes of DNA, RNA, and proteins (2–4).

Despite these successes, FRET has had a number of serious flaws which has limited its utility. First, the maximum distance which can be measured has been less than optimal for many biological applications. Second the lifetime of commonly used donor fluorophores are short (typically a few nanoseconds) and multiexponential, making lifetime measurements difficult and of limited accuracy. Third, the signal-to-background of the sensitized emission has been low due to interfering fluorescence from the donor and from direct excitation of the acceptor. Fourth, precise distances have been difficult to determine because the efficiency of energy transfer depends not only on the $R^{-6}$ distance between the donor and acceptors, but also on their relative orientation, as expressed by the $\kappa^2$ factor. (The efficiency of energy transfer=$1/(1+R^6/R_o^6)$, where $R_o$ is a function of $\kappa^2$ :see Appendix).

The luminescent lanthanide elements terbium and europium are attractive FRET donors because they potentially overcome many of these problems. Because lanthanide emission does not arise from a singlet to singlet transition, energy transfer using lanthanide donors is more accurately called luminescence resonance energy transfer (LRET). The lanthanides have primarily been used in diffusion-enhanced FRET (5) and as isomorphous replacements in calcium-binding proteins (6–8). In addition, Mathis has used europium cryptates with the multichromophoric Allophycocanin to achieve an extremely large $R_o$ of 90 Å (9). We have recently presented results showing numerous advantages of using a polycarboxylate-chelate of europium as a donor in conjunction with an organic dye such as CY-5 as the acceptor (10). Here we extend these results to the use of terbium as a donor.

As a model system, we covalently attach donor and acceptor to the 5' ends of a series of double-stranded DNA oligomers of varying length. The use of DNA in such a model system has been previously shown to be valid for energy transfer measurements between organic dyes (11).

MATERIAL AND METHODS

Synthesis of Labeled DNA Oligomers. Complementary DNAs of 10, 12, 14 bases in length were synthesized using standard phosphoramidite procedures. An amino-group attached via a six-carbon linker (Glen Research) was incorporated at the 5' end. The acceptor sequence was that used by Clegg et al (11): 5'-CCA-CTC-TAG-G-3'SEQ ID NO:01(10 bp);5'-CCA-CTG-GCT-AGG-3'SEQ ID NO:02(12 bp);5'-CCA-CTG-CTG-CTA-GG-3'SEQ ID NO:3'(14 bp). The 5-isomer of Tetramethylrhodamine-isothiocyanate (Molecular Probes. T-1480: abbreviation: TMR) was attached via standard procedures and purified by reverse phase HPLC. Extinction coefficients for TMR attached to DNA were determined to be $e_{260}=33$ mM$^{-1}$cm$^{-1}$. The donor-strand consisted of complementary DNA labeled at the 5' end with a terbium chelate. The chelate is diethylenetriaminetetraacetic acid coupled to a laser dye, carbostyril 124 (DTPA-cs124). Details of the donor chelate synthesis will be presented elsewhere. Unlabelled DNA oligomers were also synthesized.

Hybridization Conditions:

Donor and acceptor strands were mixed in desired ratio in a $D_2O$-based buffer containing 10 mM Tris, pH 8.0, 10 mM $MgCl_2$, 150 mM NaCl. Experiments were also performed in an $H_2O$-based buffer. Donor strand concentration was approximately 200 nM. Oligomers were annealed by heating to 75° C. and cooled to the final temperature (22° C. or 5° C.) over 15 minutes.

Spectroscopy:

Absorption measurements were made on a Hewlett Packard 8452A spectrometer. Steady-state fluorescence measurements were on a SPEX Fluorolog fluorimeter. Time-resolved and gated luminescence measurements were made on a laboratory-built spectrometer utilizing right-angle detection with a pulsed Laser-Photonics Nitrogen laser (5 nsec pulse width, 40 Hz repetition rate), a Gallium-arsenide photon-counting detector, a gated discriminator (Ortec 584) and a multichannel scalar with 2 μsec time-resolution. Polarization studies were also conducted although energy-transfer experiments performed without an analyzer gave the same results as those using an analyzer. An analyzer was therefore routinely omitted. A temperature-regulated cuvette-holder and a quartz 3 mm×3 mm cuvette was used. Lifetime data was fit using TableCurve software (Jandel Scientific).

Results and Discussion

The structure of the donor chelate, DTPA-cs124-Tb, and the model system used for energy transfer is shown below:

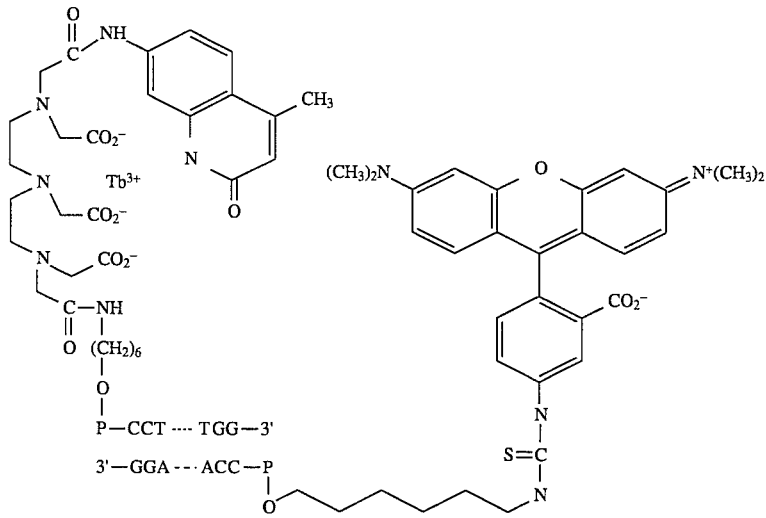

The donor-chelate has several important features. First, the chelate binds terbium (and europium) extremely tightly—titration with a 100 fold excess of EDTA ($K_b<10^{17}M^{-1}$) is unable to displace a measurable amount of terbium. This is in agreement with other DTPA-based chelators (12) and ensures that there is no free terbium. Second, the chelate allows site-specific attachment of, terbium to macromolecules. Third, the chelate shields the terbium from non-radiative dexcitation mechanisms, likely resulting in a quantum yield for terbium luminescence near unity in $D_2O$ (see Appendix I). Finally, the covalent attachment of the laser dye carbostyril 124 overcomes the extremely low absorption cross-section of terbium ($<1M^{-1}cm^{-1}$) (6). The cs124 absorbs light ($\epsilon_{328}=11,000M^{-1}cm^{-1}$; $\epsilon_{338}=8,000M^{-1}cm^{-1}$) and because of its close proximity to the terbium, transfers energy to the lanthanide (13, 14).

FIG. 1 shows the spectral characteristics of the terbium chelate and the tetramethylrhodamine which lead to efficient energy transfer and a large $R_o$ of 65 Å in $D_2O$ (60 Å in $H_2O$). $R_o$ is calculated from standard equations (see appendix). Here we mention two unusual aspects of using a lanthanide chelate as donor: 1) The efficiency of energy transfer can be adjusted, and hence $R_o$ optimized for the particular system being measured, simply by varying the ratio of $H_2O$ to $D_2O$ in the solvent. The $H_2O$/$D_2O$ ratio affects the efficiency of energy transfer by altering the lanthanide quantum yield ($q_D$) in our chelate ($q_D\approx1$ in $D_2O$; $q_D\approx0.6$ in $H_2O$; see Appendix I) (15). 2) The orientation dependence of the energy transfer process is minimized because the terbium has multiple, degenerate, electronic transitions and is therefore an isotropic donor, even if stationary. This minimizes uncertainty in the measured distance due to orientation effects of +/−12 % in the worst case(16).

FIG. 1 also shows the highly spiked nature of the terbium emission. Donor quenching can be measured without interference from acceptor emission at 492 nm and 546 nm. Similarly, the sensitized emission of the acceptor can be measured without significant interference from donor luminescence because terbium is nearly silent around 570 nm, where TMR is at 70% of its emission maximum. The terbium signal at 570 nm is 240× less than at its maximum, 546 nm.

When measuring the sensitized emission, we can also eliminate the direct fluorescence of the acceptor by temporal discrimination. We use pulsed excitation, and collect data only after a 90 μsec delay, during which time direct fluorescence of the rhodamine has decayed away. (The acceptor fluorescence, with a lifetime of a few nanoseconds, decays rapidly; we also find a small component—probably either delayed fluorescence or a detector artifact—which decays away within the 90 μsec delay.) The donor, because of its millisecond lifetime, stays excited and capable of transferring energy at the end of the delay period. Consequently, any signal arising around 570 nm after the delay is due only to sensitized emission, i.e. fluorescence of the acceptor due to energy transfer.

Figure 2A:
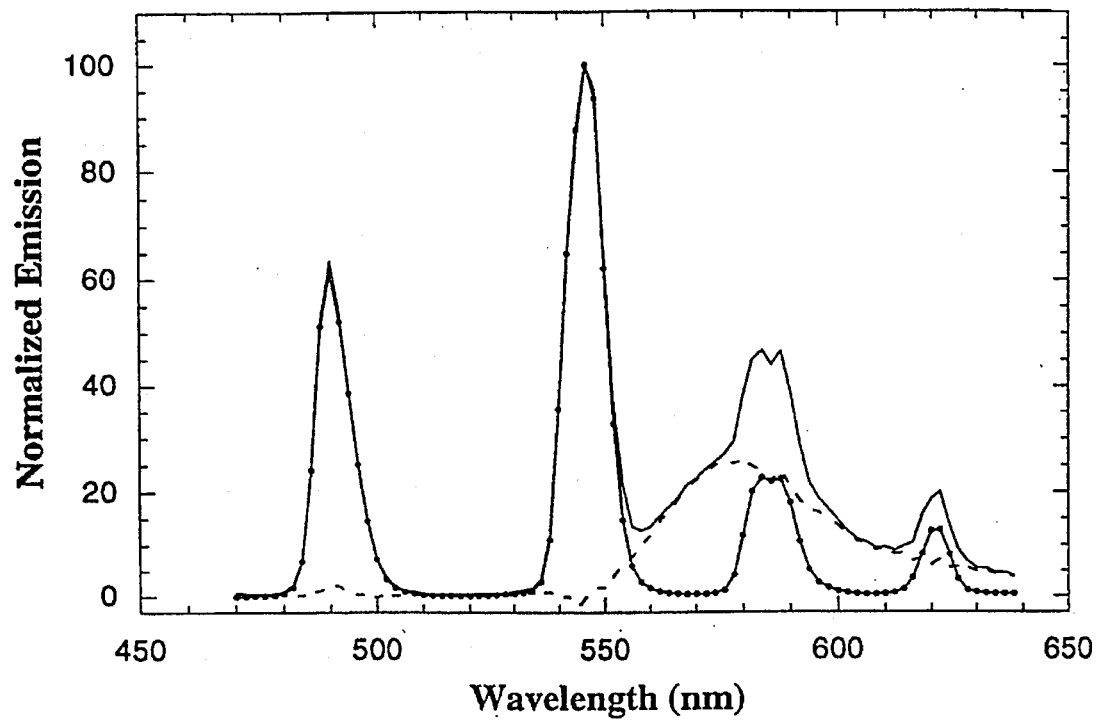
FIG. 2A: Emission spectrum of a donor-only labelled dsDNA (solid curve with circles), a donor-acceptor labelled dsDNA (solid curve), and the difference spectra (dashed curve). The DNA length is 10 bp in all cases. The donor-only curve and donor-acceptor curves are normalized at 546 nm. In the donor-acceptor complex, the ratio of donor-strand DNA to acceptor strand is slightly greater than 1, although FIG. 3, curve C, shows that approximately 12% of the donor strand is unhybridized. The signal is collected with a 7.5 msec gate after a 90 msec delay. Data collected with a 150 msec. delay was very similar. The 54:1 signal to background of the donor-acceptor curve at 570 nm is calculated by dividing the donor-acceptor signal at 570 nm by the donor-only signal at 570 nm. The latter is calculated by dividing the donor-only signal at 546 nm by 240. Background due to detector noise, direct acceptor fluorescence or photon statistics are not significant. The difference spectra represents the sensitized emission. As expected, the shape is nearly identical to that of a TMR-only labelled DNA fluorescence spectrum.

FIG. 2A shows the results of an energy transfer experiment on a partially hybridized 10 mer DNA. The average energy transfer is 77%. The signal to background of the sensitized emission at 570 nm is 54:1. By comparison, the signal to background for sensitized emission when using fluorescein-rhodamine as energy transfer pairs on the same DNA is approximately 1. Because the background is so small in our case, small signals become measurable, and hence distances much greater than $R_o$ are expected to be possible. Horrocks and Bruno, for example, have shown the ability to measure distances of $4R_o(R_o=3.1$ Å) utilizing the dark-background sensitized emission of tyrosine to terbium energy transfer (6).

We can isolate the sensitized emission signal from donor luminescence even in regions where donor luminescence is significant. In a procedure analogous to that used by Clegg et al (11), we can subtract the donor luminescence at all wavelengths, leaving the sensitized emission signal. The efficiency of energy transferred is then simply the area of the corrected sensitized emission, divided by the total corrected area:

$$\text{efficiency of energy transfer} = (f_A/q_A)/(f_A/q_A+f_D) \quad (1)$$

where $f_A$ is the area under the sensitized emission curve, $q_A$ is the fluorescence quantum yield of the acceptor, and $f_D$ is the area under the donor luminescence curve. One can determine the quantum yield of the acceptor by a comparison with the donor quenching data. Based on a quantum yield of 0.174 for TMR (see Appendix II), equation 1 yields an avenge energy transfer of 77 %.

Figure 2B:
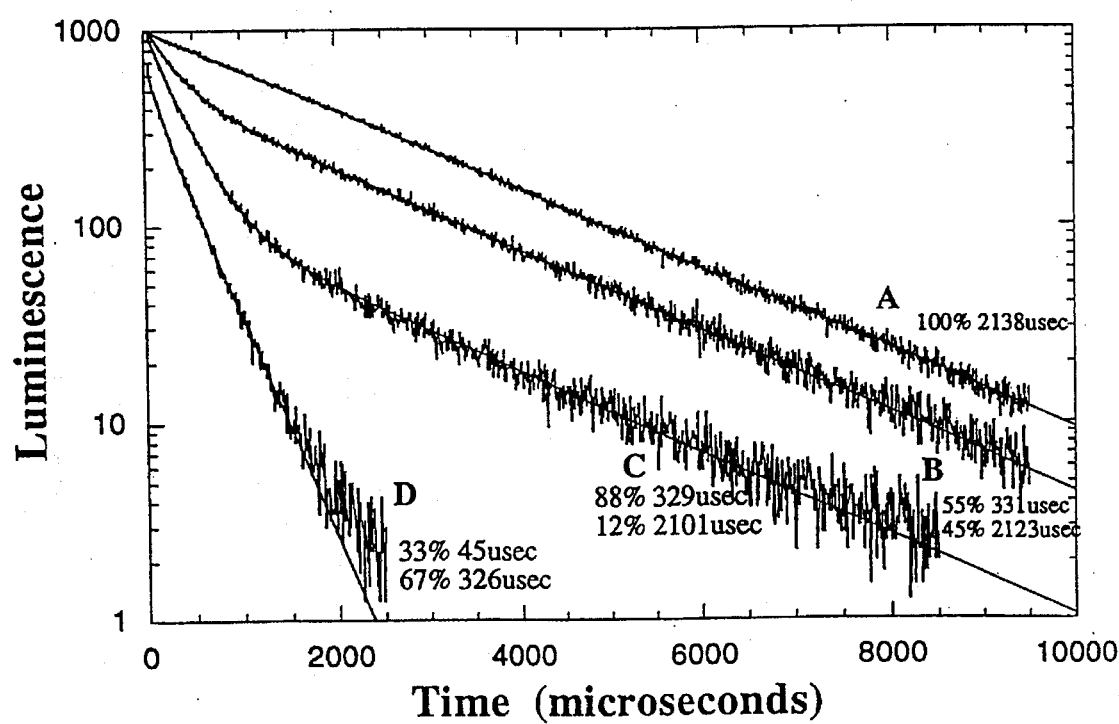
FIG. 2B: Donor lifetime-quenching at 546 nm on a donor-only labelled 10 mer ssDNA (curve A), a series of partially hybridized donor-acceptor 10 mer DNA oligomers (curves B and C), and the sensitized emission signal at 570 nm (curve D) corresponding to curve B. To generate curves B and C, a single-stranded donor-only DNA (top curve) was titrated with increasing amounts of acceptor-labelled complement and annealed. The solid line through each curve is a two-exponential (four parameter) fit to the data. The percentages of each component represent their amplitude, e.g. curve B is fit to the equation $y=55\%\exp(-t/331 \text{ msec})+45\%\exp(-t/2123 \text{ msec})$, indicating 55% donor-acceptor complex, and 45% donor-only complex. $r^2$ residuals in all cases >0.99 and for donor-quenching curve showed no structure. Sensitized emission curve showed residual structure at >1.5 msec possibly due to a small amount ($\leq 1\%$) of signal arising from unquenched donor species.

FIG. 2B shows the lifetime data on a series of 10 mer DNA oligomers. The donor-only (single stranded DNA) signal is single exponential with a lifetime of 2.14 msec. (A terbium labeled DNA oligomer hybridized to its complement is single exponential with a lifetime of 2.80 msec. The difference in lifetime between double-stranded and single-stranded terbium-only DNA is likely due to different radiative rates arising from different symmetries surrounding the terbium, rather than different quantum yields.) A titration with increasing amounts of acceptor strand shows bi-exponential donor quenching (curves B and C). The long-lifetime component corresponds to unhybridized, donor-only single stranded DNA; the short component corresponds to those terbium-strands that are hybridized with acceptor strands. As expected, increasing the amount of acceptor strand increases the amplitude of the short component and decreases the amplitude of the long component, while leaving their lifetimes unchanged (compare curves B and C). That the long-time component equals the donor-only signal is an important internal control which shows that intermolecular energy transfer is not significant. The lifetime of the short component corresponds to an energy transfer in the donor-acceptor complex of 88% (1−331 μsec/2809 μsec). By comparison, the energy transfer on the same 10 mer DNA with the same six-carbon linkers using fluorescein-TMR pair is 23%. (11)

In calculating the efficiency of energy transfer based on the sensitized emission curve, we ignore the short time component since this is due to residual signal arising from the direct fluorescence of the acceptor. (No gate was used for this data). Multiple experiments show the long-time component is repeatable to within 10% in the worst case, and usually repeatable within a few percent. The short-time component, however, is highly variable since there is a very large, very short spike due to direct fluorescence which cannot be resolved.

At two-fold excess of acceptor strand, there is still a 10–12% unhybridized component. A similar phenomenon has been seen with dye-labelled oligomers (17) and in FRET experiments with europium substituted in our chelate (10). In our case it does not appear to be a simple melting-temperature phenomenon since it is present at both 5° C. and 22° C. The reason for this is under investigation. It is unlikely that this residual unquenched donor signal is due to fundamental lanthanide photophysics since this would require an uncoupled magnetic dipole transition, a situation which is not present since all terbium (and europium) luminescence arises from the same excited state (18, 19).

FIG. 2B also shows the lifetime of the sensitized emission at 570 nm corresponding to the biexponential donor-quenching (curve B). The sensitized emission decay can be accurately fit to the equation: $y=33\%\exp(-t/45\ \mu sec)+67\%\exp(-t/326\mu sec)$. The 45 msec component corresponds to direct fluorescence from the acceptor or a detector artifact (which can be eliminated by gating). The 326 μsec component is due to energy transfer on the donor-acceptor complex, and agrees extremely well with the 329–331 μsec donor quenching component. Note that after approximately 90 μsec, the only species which contribute to the sensitized emission signal is the donor-acceptor complex—donor-only or acceptor-only do not contibute. This significantly minimizes the problem of incomplete labeling. The sensitized-emission lifetime signal is also insensitive to total concentration, to quantum yields, and to non-energy-transfer effects which can cause donor quenching.

Table 1 summarizes the lifetime and energy transfer data on donor-acceptor labelled DNA duplexes of 10,12 and 14 bp length.

TABLE I

|  | Lifetime (μsec) | Efficiency of energy transfer | Calculated Distance (Å) | Clegg et al. Distance (Å) |
|---|---|---|---|---|
| 10mer | 336 | 0.88 | 46.6 | 55.5 |
| 12mer | 724 | 0.74 | 54.6 | 56.4 |
| 14mer | 1154 | 0.59 | 61.2 | 61.0 |

Data from multiple experiments show donor quenching and sensitized emission lifetimes for a given length DNA agree always within 10%, usually within a few percent. As expected, there is a decrease in energy transfer with increasing distances. For comparison we include the distances determined by Clegg et al. using fluorescein-TMR (11). Both results are consistent with the DNA double-helix geometry, although differing salt conditions and donor-lifetimes lead to different dye positions, and hence different measured distances. We have fit our distances using the Clegg et al. model of the DNA helix and attached dyes. With only three data points, it is not possible to resolve uniquely all the parameters in the model, but nevertheless, a good fit to their model is achieved if it is assumed that the terbium chelate and/or acceptor are fairly close to the DNA helix. This reduces the modulation seen in their FRET data, which arises because of the helical geometry of the DNA and the fact that their donor and acceptor are extended away from the helix (19 Å and 13 Å, respectively). This difference is qualitatively reasonable since the long-lifetime of our donor is expected to allow constrained diffusion of the donor and acceptor within the limits placed by the six-carbon linkers, and because of the greater ionic strength used here, which minimizes charge repulsion.

In summary, the data are consistent with the geometry of the double-helix DNA if the energy transfer data are derived based on the dipole-dipole Förster-type mechanism. Numerous technical advantages of luminescence resonance energy transfer make this a technique well suited for measurements on biologically interesting macromolecules.

Appendix I

Calculation of $R_o$: $R_o$, the distance at which 50% of the donor's excited state energy is transferred to the acceptor, is calculated from standard equations (1):

$$R_o = (8.79 \times 10^{-5} J \kappa^2 n^{-4} q_D)^{1/16} \text{Å} \quad (2)$$

where $q_D$ is the luminescence quantum yield for donor emission in the absence of acceptor, J is the spectral overlap of the donor emission ($f_D$) and acceptor absorption ($e_A$) ($J = \int f_D \epsilon_A \lambda^4 d\lambda$), n is the index of refraction and $k^2$ is a geometric factor related to the relative angles of the two dipoles. Here we evaluate each of the terms in equation 2 and discuss their uncertainty.

The index of refraction, n, varies from 1.33 for water to 1.39 for many organic molecules. We have used 1.33. A numerical integration leads to a J overlap integral of $3.8 \times 10^{15}$ nm$^4$M$^{-1}$. This is an upper limit for J since the 546 nm peak of terbium may arise from magnetic dipole, as well as electric dipole transitions (19), and the former do not significantly transfer energy (18). The fraction of magnetic dipole contribution can be calculated theoretically (20, 21), or the problem avoided by using the 492 nm line of terbium, which is known to be solely an electric dipole transition (20).

When using organic dyes in FRET, $\kappa^2$ is often a significant source of uncertainty and in the worst case, may vary from 0 to 4 (22). With terbium, however, emission arises from multiple electronic transitions which constrain $\kappa^2$: $\frac{1}{3} < \kappa^2 < \frac{4}{3}$. In addition, it is likely that the acceptor can undergo rotational motion during the millisecond donor-lifetime. This further constrains $\kappa^2$ and we assume $\kappa^2 = \frac{2}{3}$, corresponding to a random orientation rotating rapidly within the donor lifetime.

The luminescence quantum yield of the terbium, $q_D$, is difficult to accurately determine because of terbium's intrinsically low absorbance. $q_D$, however, is likely very close to 1 in $D_2O$ (see below). Note that when calculating $R_o$, it is important to use the terbium quantum yield ($\approx 1$ in $D_2O$), not the quantum yield of the entire chelate. The quantum yield of the entire chelate equals the lanthanide quantum yield times the fraction of energy absorbed by the cs124 that is transferred to the lanthanide.

Quantum yield of lanthanide emission: There are several lines of (indirect) evidence which argue $q_D \approx 1$ in $D_2O$. First, emission arises from 4f—4f inner shell electrons which are shielded from the solvent and other sources of non-radiative deexcitation by the chelate. The 1.2 $H_2O$ molecules in the primary coordination sphere of the terbium in our chelate (data not shown) are the primary source of non-radiative deexcitation, but these are replaced by $D_2O$, which do not significantly deactivate terbium (15, 23). The nonwater ligands, carboxylate groups and amine nitrogens are extremely inefficient at deactivating the terbium excited state (23). Via temperature studies (24), we have also looked for quenching effects of the cs124 and have found none.

A second line of evidence supporting $q_D \approx 1$ in $D_2O$ comes from the work of Elbanowski and coworkers who directly measured the quantum yield of a 1:3 mixture of terbium: EDTA in $H_2O$, and found a value of 0.54 (25). This measurement is difficult and of unknown accuracy, but nevertheless, it suggests a high quantum yield even in $H_2O$, and the quantum yield in $D_2O$ is expected to be considerably higher. (There are probably 2 water molecules coordinated to the terbium in their complex (23)).

The third line of evidence comes from energy transfer experiments using terbium as a donor in thermolysin (8, 26), and as an acceptor in invertebrate calmodulin (6), where the assumption (sometime implicit) of unity quantum yield in $D_2O$ gives good agreement with x-ray crystallography data.

Appendix II

Calculating the fluorescence quantum yield of the acceptor: By comparing the donor-quenching lifetime data with the areas and using equation 1 it is possible to measure the quantum yield of the acceptor. This is a general and new method for measuring quantum yields of any dye whose absorption overlaps the emission of terbium (or europium). It has the advantage over more conventional methods of measuring quantum yields in that the measurement involves only one sample—the actual sample of interest—rather than comparing a reference to the sample.

To evaluate the quantum yield of TMR, we assume the unknown in equation 1 is $q_A$ and take the average efficiency of energy transfer to be 77.6 %, as determined from curve C (supra). Based on the integrated areas (620 for $f_A$ and 1032 for $f_D$, in arbitrary units), this yields $q_A$=0.174. By comparison, free tetramethylrhodamine in phosphate-buffered saline has a quantum yield of 0.25, as measured by standard techniques (27).

Parenthetical References of Example 1

1. Cantor, C. R. Schimmel, P. R. (1980) *Biophysical Chemistry*. (W. H. Freeman and Co., San Francisco).
2. Clegg, R. M. (1992) *Methods Enzymol.* 211, 353–388.
3. Selvin, P., R. (1994) *Methods Enzymol.* 246. (in press).
4. Coker, G., III, Chen, S. Y. & van der Meer, B. W. (1994) *Resonance Energy Transfer*. (VCH Publishers, Inc.) (in press).
5. Stryer, L., Thomas, D. D. & Meares, C. F. (1982) *Annu. Rev. of Biophys. and Bioengin.* 11, 203–222.
6. Bruno, J., Horrocks, W. D., Jr. Zauhar, R. J. (1992) *Biochem.* 31, 7016–7026.
7. Cronce, D. T. Horrocks, W. D., Jr. (1992) *Biochem.* 31, 7963–7969.
8. Horrocks, W. D., Jr., Holmquist, B. Vallee, B. L. (1975) *Proc. Natl. Acad. Sci. USA* 72, 4764–4768.
9. Mathis, G. (1993) *Clin. Chem.* 39, 1953–1959.
10. Selvin, P. R., Rana, T., M. & Hearst, J. E. (1994) *JACS* (in press)
11. Clegg, R. M., Murchie, A. I., Zechel, A. & Lilley, D. M. (1993) *Proc. Natl. Acad. Sci., USA* 90, 2994–2998.
12. Oser, A., Collasius, M. Valet, G. (1990) *Anal Biochemistry* 191, 295–301.
13. Abusaleh, A. Meares, C. (1984) *Photochem. & Photobiol.* 39, 763–769.
14. Kirk, W. R., Wessels, W. S. Prendergast, F. G. (1993) *J. Phys. Chem.* 97, 10326–10340.
15. Horrocks, W. D., Jr., Schmidt, G. F., Sudnick, D. R., Kittrell, C. Bernheim, R. A. (1977) *JACS* 99, 2378–2380.
16. Stryer, L. (1978) Ann. Rev. Blochem. 47, 819–46.
17. Cooper, J.P. Hagerman, P. J. (1990) *Biochemistry* 29, 9261–9268.
18. Dexter, D. L. (1953) *J. Chem. Phys.* 21, 836–850.
19. Bunzli, J.-C. G. (1989) in *Luminescent Probes*, ed. Bunzli, J.-C. G., Choppin, G.R. (Elsevier, New York), pp. 219–293.
20. Carnall, W. T., Fields, P. R. Rajnak, K. (1968) *J. Chem. Phys.* 49, 4412–4423.
21. Gorller-Walrand, C., Fluyt, L., Ceulemans, A. Carnall, W. T. (1991) *J. Phys. Chem.* 95, 3099–3106.
22. Dale, R. E., Eisinger, J. Blumberg, W. E. (1979) *Biophys. J.* 26, 161–194.
23. Horrocks, W. D., Jr. Sudnick, D. R. (1979) *J. Am. Chem. Soc.* 101, 334–350.
24. Alpha, B., Ballardini, R., Balzani, V., Lehn, J.-M., Perathoner, S. & Sabbatini, N. (1990) *Photochem. and Photobiol.* 52, 299–306.
25. Elbanowsld, M., Lis, S. & Konarski, J. (1989) *Monat. Chem* 120, 699–703.
26. Berner, V. G., Dainall, D. W. Birnbaum, E. R. (1975) *Biochem. & Biophys. Res. Commun.* 66, 763–768.
27. Waggoner, A. (1994) *Methods Enzymol.* 246 (in press).

Example 2

In this example, we exemplify the technique of fluorescence resonance energy transfer (FRET) by introducing a europium chelate as donor and an organic dye, CY-5 as acceptor. The use of lanthanide donors, in general, and this pair, in particular, has many advantages over more conventional FRET pairs which rely solely on organic dyes. The $R_o$ is large, 70 Å; the donor lifetime is single exponential and long (2.5 msec in $D_2O$); the orientation factor which creates uncertainty in measured distances is minimized by the donor's multiple electronic transitions and long lifetime; the sensitized emission of the acceptor can be measured with little or no interfering background, yielding a>50 fold improvement in signal to background over standard donor-acceptor pairs. This improvement in signal to background is expected to make distance measurements of greater than 100 Å feasible. We also measure the sensitized emission lifetime, a measurement which is independent of total concentration and incomplete labeling.

We have used a luminescent europium chelate as donor and an organic dye, CY-5 as acceptor. This luminescence resonance energy transfer (LRET) has several advantages over the more conventional FRET[2]. The distance at which 50% of the energy is transferred ($R_o$) is large, 70 Å; the donor lifetime is single exponential and long (0.63 msec in $H_2O$; 2.5 msec in $D_2O$), making lifetime measurements facile and highly accurate; the orientation dependence ($\kappa^2$) of energy transfer is minimized by the donor's multiple electronic transitions and long lifetime, limiting uncertainty in the measured distance due to orientation effects to +/–12% in the worst case[3]; the sensitized emission of the acceptor can be measured with little or no interfering background, yielding a>50 fold improvement in signal to background over standard donor-acceptor pairs and enabling distances several times $R_o$ to be measured[4]. We also measure the sensitized emission lifetime which, in our case, is independent of total concentration and incomplete labeling.

We have used both terbium[5] and europium as donors, and the results for europium are presented here. A schematic diagram of the donor-acceptor model system comprising double stranded DNA with europium chelate (donor) at one 5' end and CY-5 at other 5' end is shown below:

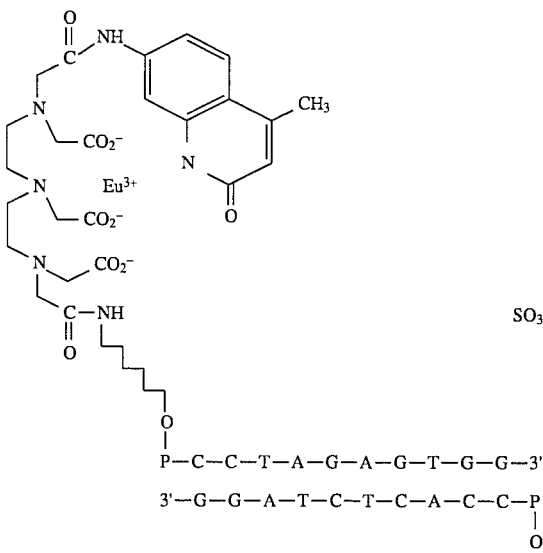
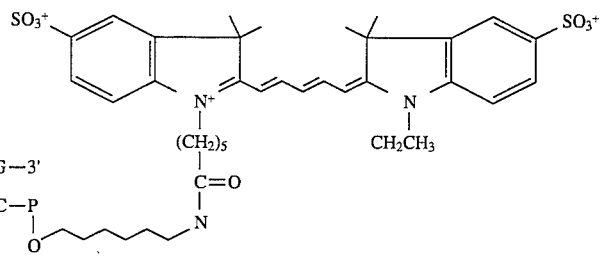

SEQ ID NO: 19

```
P—C—C—T—A—G—A—G—T—G—G—3'
3'—G—G—A—T—C—T—C—A—C—C—P
```

The europium chelate, (diethylenetriaminepentacetic acid-carbostyril 124-Eu :trivial name, DTPA-cs124-Eu) was made by a modification of the procedure of Bailey[12], starting with the dianhydride of DTPA (Sigma), carbostyril 124 (Aldrich), and the synthetic DNA base-protected and on the column to ensure that labelling occurs only at the 5' amino group. The cs124 effectively increases the absorption cross section of the europium to approximately $8000M^{-1}cm^{-1}$ at 337 nm, where we excited the donor with a pulsed Nitrogen laser. A 100-fold excess of EDTA did not remove any noticeable mount of europium from the DTPA-cs 124 chelator. The acceptor was 5' labeled with CY-5[13] (Biological Detection Systems) via standard methods. Unlabelled complementary DNA oligomers were made as controls. All DNA was reversed-phase HPLC purified. In this system, the double-stranded DNA oligomer serves as a rigid tether to establish a defined distance between the europium donor and the CY5 acceptor. The points of attachment of the donor and acceptor are separated by 42 Å, although the dye positions retain limited variability due to the flexible six-carbon linkers used for attachment[6,7].

Figure 3:
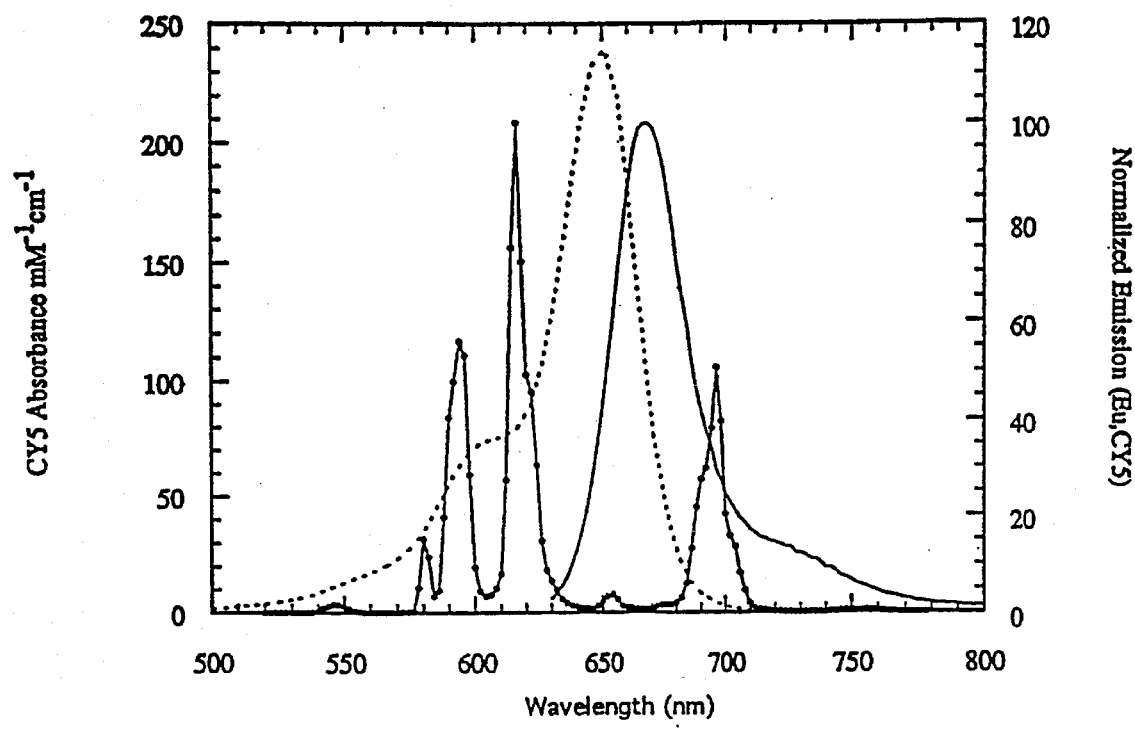
FIG. 3: Spectra of DNA labelled with either CY-5 or DTPA-cs124-Eu. Dashed and solid lines are the absorption and emission spectra of CY-5, respectively. Solid line with circles is the emission spectrum of DTPA-cs124-Eu on DNA. The small signal at 548 nm is due to contaminating terbium. All data shown are at 0.5 mM donor strand concentration in 10 mM Tris-HCl pH 8.0, 10 mM $MgCl_2$, 150 mM NaCl, $D_2O$ at 5° C. Decreasing concentration by 2 and 4 fold yielded the same results. Emission spectroscopy was done on a laboratory-built spectrometer utilizing a pulsed Nitrogen laser, photon-counting detector and a multichannel scalar with 2 msec time-resolution. The CY-5 emission spectrum shown above was obtained on a steady-state SPEX fluorimeter.

FIG. 3 shows the spectral characteristics which lead to the unusually large $R_o$ of 70 Å in $D_2O$ (56 Å in $H_2O$). $R_o$ is determined from standard equations[1] based on a calculated spectral overlap (J) of $6.55 \times 10^{15} M^{-1} nm^4$, an orientation factor ($\kappa^2$) of $\frac{2}{3}$, an index of refraction of 1.33, and a quantum yield for europium luminescence in $D_2O$ of one (0.25 in $H_2O$)[8]. In calculating $R_o$ it is important to use the quantum yield of the lanthanide emission, and not the quantum yield of the entire chelate, and to include in the spectral overlap (J) calculation only those transitions which are electric dipole. The europium emission at 617 nm, which is used here for energy transfer, has been shown to be "forced" electric dipole[9], and hence Förster's theory of energy transfer is applicable. The europium emission at 596 nm cannot couple to an acceptor because it is a magnetic dipole transition and so is not included in the spectral overlap calculation[10].

We can measure the sensitized emission of the acceptor without significant interference from either donor emission or direct acceptor fluorescence. At 668 nm, europium is nearly silent (europium emission at 668 nm is 125 times less than at its 617 nm maximum) and by using pulsed-excitation and gating off the detector for 90 msec, the direct fluorescence of the carbostyril sensitizer in the donor complex and the direct fluorescence of the CY-5 are completely eliminated, while the europium stays excited and capable of energy transfer[11].

Figure 4A:
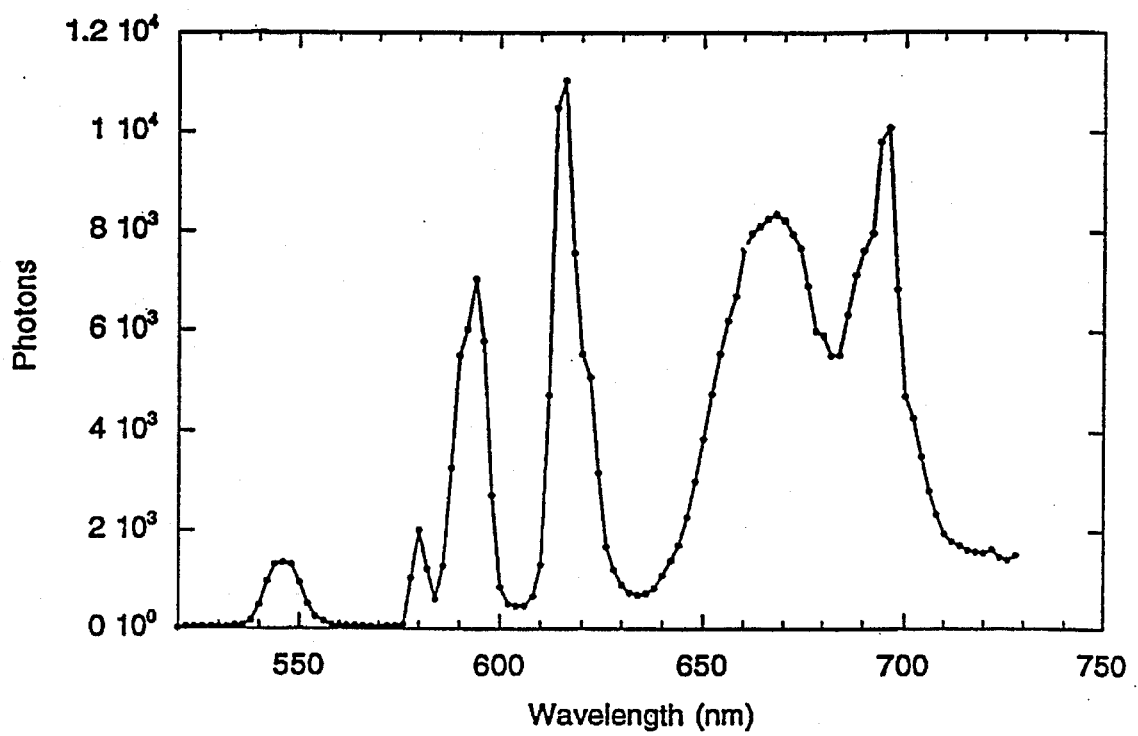
FIG. 4A Emission spectrum of a mixture of donor-strand DNA and acceptor strand in approximately 1:0.6 ratio. The signal is collected with a 7.5 msec gate after a 90 msec delay.

FIG. 4A shows such a dark-background sensitized emission experiment. Here the ratio of donor to acceptor strands is approximately 1:0.6; we intentionally add less acceptor than donor to show the ability of our system to analyze heterogeneous signals. The average fraction of energy transfer in FIG. 4A is 57 %. The signal at 668 nm arises from sensitized emission of CY-5, i.e. fluorescence due only to energy transfer. We calculate the signal/background at 668 nm to be 94:1 (where background is due to a small mount of europium luminescence), a factor of 50–100 improvement in signal/background over the sensitized emission signal from fluorescein-rhodamine, one of the best donor-acceptor pairs, attached to the same 10 mer.

Figure 4B:
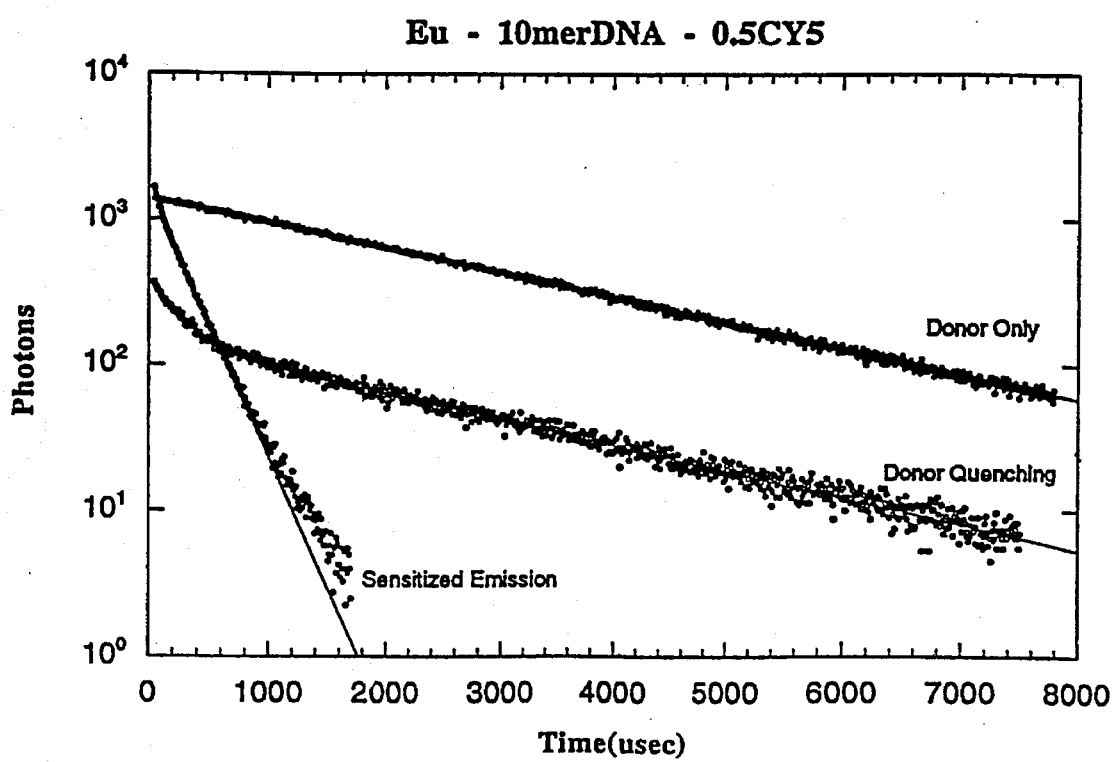
FIG. 4B Lifetime data corresponding to FIG. 3, showing donor-only lifetime of 2.5 msec, a biexponential donor-quenching corresponding to a mixture of donor-only and donor-acceptor complexes, and a largely single exponential sensitized emission signal. The latter signal is insensitive to donor-only or acceptor-only species. Donor-only lifetime on single-stranded and double-stranded DNA differ by less than 5%.

FIG. 4B shows lifetime data corresponding to FIG. 4A. The donor-only signal is single exponential with a lifetime of 2.52 msec. The donor quenching signal fits a biexponent extremely well ($r^2$=0.998): y=63 %exp(–t/0.22 msec)+ 37%exp(–t/2.40 msec.) The long-time component corresponds to the donor-only species. That the long-time component nearly equals the donor-only lifetime is an internal control which shows that intermolecular energy transfer is at most 5%. The short time component arises from into molecular energy transfer in the hybridized donor-acceptor complex and corresponds to 91% quenching (1–0.22 msec/ 2.52 msec), and a donor-acceptor distance of 46 Å. (Fluorescein-rhodamine on the same DNA with C-6 linkers yields 22% energy transfer[7].) A titration with increasing acceptor concentration increases the fraction of the short time-component but does not change its lifetime, as expected. At two-fold excess of acceptor strand, a 10% component corresponding to donor-only signal remains, presumably due to unhybridized donor strands.

FIG. 4B also shows the lifetime of the sensitized emission. The sensitized emission lifetime signal is fit to a biexponential ($r^2$=0.999): y=40%exp(–t/59 μsec) +60%exp(–t/0.25 msec). The short-time component is due to direct fluorescence of the acceptor and can be eliminated by gating the detector. The 0.25 msec component is due to an energy transfer of 90% (1–0.25/2.52 msec), in excellent agreement with the short-time component of the donor quenching. A very small long-time component (≈1%) can be seen due to direct donor fluorescence.

In summary, luminescence energy transfer yields results consistent with a Förster theory assuming the appropriate parameters are used. Based on the large $R_o$, the ease and reproducibility of our lifetime measurements, and the excellent signal to background, distances significantly greater than 100 Å are measurable.

FOOTNOTED REFERENCES IN EXAMPLE 2

(1) Cantor, C. R.; Schimmel, P. R. *Biophysical Chemistry*; W. H. Freeman and Co.: San Francisco, 1980; Vol. 2.
(2) Lanthanides in energy transfer have been used in diffusion enhanced FRET (Stryer, L.; Thomas, D. D.; Meares, C. F. In *Annual Review of Biophysics and Bioengineering*; L. J. Mullins, Ed.; Annual Reviews, Inc.: Palo Alto, Calif., 1982; Vol. 11; pp 203–222). They have also used been used with multichromophoric Allophycocanin (Mathis, G. *Clin. Chem.* 1993, 39, 1953) and as isomorphous replacements in calcium-binding proteins (Horrocks, W. D., Jr.; Holmquist, B.; Vallee, B. L. *Proc. Nat. Acad. Sci. USA* 1975, 72, 4764; Cronce, D. T.; Horrocks, W. D., Jr. *Biochem.* 1992, 31, 7963).
(3) Stryer, L. *Ann. Rev. Biochem.* 1978, 47, 819–846.
(4) The ability to measure energy transfer beyond $R_o$ using sensitized emission has been shown by Bruno and Horrocks. They used terbium as the acceptor and tyrosine as the donor. With an $R_o$ of 3 Å they measured out to 12 Å. (Bruno, J.; Horrocks, W. D., Jr.; Zauhar, R. J. *Biochem.* 1992, 31, 7016.)
(5) Selvin, P. R.; Hearst, J. E. *Proc. Natl. Acad. Sci, USA* 1994 (submitted),
(6) Cardullo, R.; Agrawal, S.; Flores, C.; Zamecnik, P. C.; Wolf, D. E. *Proc. Natl. Acad. Sci., USA* 1988, 85, 8780.
(7) Clegg, R. M.; Murchie, A. I.; Zechel, A.; Lilley, D. M. *Proc. Natl. Acad. Sci. USA* 1993, 90, 2994.
(8) The exact quantum yield is difficult to determine although the long-lifetime and lack of radiationless deactivation mechanisms make it likely that the quantum yield is close to one in $D_2O$. This assumption has given distances in agreement with x-ray crystallography studies (See ref 4). In $H_2O$, the quantum yield is decreased because there are 1.3 water molecules in the primary coordination sphere of the lanthanide in our chelate (Horrocks, W. D., Jr.; Sudnick, D. R. *J. Am. Chem. Soc.* 1979, 101, 334).
(9) Bunzli, J.-C. G. In *Lanthanide Probes in Life, Chemical and Earth Sciences, theory and Practice Luminescent Probes*; Bunzli, J.-C. G. Choppin, G.R. Ed.; Elsevier: New York, 1989; pp 219–293.
(10) Dexter, D. L. *J. Chem. Phys.* 1953, 21, 836.
(11) Morrison has used gated integration to increase the signal to background of the sensitized emission with organic dyes. Morrison, L. E. *Anal. Biochem.* 1988, 174, 101.
(12) Bailey, M.P.; Rocks, B. F.; Riley, C. *Analyst* 1984, 109, 1449.
(13) Mujumdar, R. B.; Ernst, L. A.; Mujumdar, S. R.; Lewis, C. J.; Waggoner, A. S. *Bioconj. Chem.* 1993, 4, 105.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A lanthanide chelate comprising a lanthanide chelator covalently joined to a sensitizer, wherein said chelate is capable of binding a lanthanide with an equilibrium constant of at least $10^6 M^{-1}$, a complex of said chelate and said lanthanide is capable of enhanced lanthanide luminescence, and said sensitizer comprises a polynuclear heterocyclic aromatic compound of the general formula:

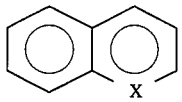

wherein X comprises an atom from periodic group 5 or 6, wherein a single position 2–8 carbon atom of said sensitizer is substituted with a linking group through which said sensitizer is covalently joined to said chelator.

2. A chelate according to claim 1, wherein a first position 2–8 carbon atom of said sensitizer is substituted with an oxygen atom through a double covalent bond, and a second position 2–8 carbon atom of said sensitizer, different than said first position 2–8 carbon atom, is substituted with a linking group through which said sensitizer is covalently joined to said chelator.

3. A chelate according to claim 2, wherein said linking group consists essentially of an mine or carboxyl group.

4. A chelate according to claim 2, wherein said first position 2–8 carbon atom is the position 2 or 4 carbon atom and said second carbon atom is the position 7 carbon atom.

5. A chelate according to claim 2, wherein a third position 2–8 carbon atom of said sensitizer, different from said first and second position 2–8 carbon atoms, is substituted.

6. A chelate according to claim 5, wherein said third position 2–8 carbon atom is the position 4 carbon and is substituted with a hydrocarbon or halogen substituted hydrocarbon.

7. A chelate according to claim 1, wherein said sensitizer comprises a 2- or 4-quinolone or a 2- or 4-courmarin.

8. A chelate according to claim 1, wherein said sensitizer comprises carbostyril 124 (7-amino-4-methyl-2-quinolone), coumarin 120 (7-amino-4-methyl-2-coumarin), coumarin 124 (7-amino-4-(trifluoromethyl)-2- coumarin), aminomethyltrimethylpsoralen.

9. A chelate according to claim 1, wherein a complex of said chelate and a lanthanide capable of binding said chelate with an equilibrium constant of at least $10^9 M^{-1}$ is capable of at least ten fold greater luminescence probability than is said lanthanide.

10. A chelate according to claim 1, wherein a first solution comprising complexes of said chelate and a lanthanide capable of binding said chelate with an equilibrium constant of at least $10^9 M^{-1}$ is capable of at least ten fold greater luminescence than is a second solution comprising said lanthanide, wherein said first and second solutions are identical except for the presence of said chelate in said first solution and absence of said chelate in said second solution.

11. A chelate according to claim 1, wherein said lanthanide is terbium or europium.

12. A chelate according to claim 1, wherein said chelator is capable of binding said lanthanide with an equilibrium constant of at least $10^{10} M^{-1}$.

13. A chelate according to claim 1, wherein said chelator comprises a plurality of carboxylate or phosphonate groups.

14. A chelate according to claim 1, wherein said chelator comprises DTPA.

15. A chelate according to claim 1, wherein said chelate is covalently joined to a macromolecule.

16. A molecular label comprising a chelate according to claim 1 covalently joined to a analyte-selective reagent.

17. A method of enhancing the luminescence of a lanthanide, said method comprising: forming a mixture of a lanthanide chelate according to claim 1 and a lanthanide capable of binding said chelate with an equilibrium constant of at least $10^{9} M^{-1}$, whereby a luminescent lanthanide chelate-lanthanide complex is formed.

18. A chelate according to claim 1, wherein said enhanced lanthanide luminescence is at least 50,000% greater intensity.

* * * * *